United States Patent [19]

Redding

[11] 4,176,542
[45] Dec. 4, 1979

[54] ANALYSIS INSTRUMENTS

[76] Inventor: Robert J. Redding, September House, Cox Green La., Maidenhead, England, S16 3EL

[21] Appl. No.: 847,604

[22] Filed: Nov. 1, 1977

[30] Foreign Application Priority Data

Nov. 2, 1976 [GB] United Kingdom ............... 45397/76

[51] Int. Cl.² ........................................... G01N 31/08
[52] U.S. Cl. ...................................... 73/23.1; 307/48
[58] Field of Search ................. 73/23, 26, 27 R, 23.1; 307/46, 48, 66; 323/15; 320/53

[56] References Cited

U.S. PATENT DOCUMENTS

| 3,449,939 | 6/1969 | Monomakhoff | 73/26 |
| 3,519,391 | 7/1970 | Winter et al. | 73/27 R X |
| 3,599,073 | 8/1971 | Wilson | 307/48 X |
| 3,955,132 | 5/1976 | Greenwood | 320/53 X |

Primary Examiner—Charles A. Ruehl

[57] ABSTRACT

Analytical devices such as chromatographs are disclosed wherein an intrinsically safe source of electrical energy is used to heat analytical elements of the devices, and optionally to power other circuits of the device.

10 Claims, 4 Drawing Figures

ANALYSIS INSTRUMENTS

This invention relates to analysis devices capable of being used in locations such as process plants or confined spaces where a hazardous atmosphere might occur. The invention is more particularly but not exclusively concerned with chromatographic analysis devices.

Laboratory based analysis devices can offer great advantages in the monitoring and control of, for example, manufacturing processes, but there are many instances where a delay in getting samples from the manufacturing area to the analysis device can reduce the effectiveness of the analysis itself and also complicate the control of the process due to the time delay. Up to the present, the adaption of analysis devices such as chromatographs for plant use has largely consisted of taking the elements of the laboratory instrument and assembling them in flameproof and air purged units in an endeavour to meet the safety regulations required for such uses.

Taking chromatographic analysis devices as an example, explosion risks in operation in a hazardous atmosphere are presented by the possibility of arcing within the electrical circuits of the device and by the high skin temperature of the chromatograph column which is often required for optimum performance of the device. Either of these could ignite a flammable atmosphere and adaptions of the device such as air purging of the device and flameproof enclosure of the electrical circuits of the device are inconvenient, bulky and expensive.

It is an object of the present invention to provide means to render analysis devices having electrical circuitry safe for use in hazardous atmospheres more simply and more cheaply than has hitherto been the case.

It is also an object of the invention to render analysis devices having hot surfaces similarly safe for use in hazardous atmospheres.

It is further still an object of the present invention to render analysis devices safe for use in hazardous atmospheres by means of avoidance of the hazard rather than trying to mitigate the consequences of the hazard.

The term "intrinsically safe" is used herein to refer to analysis devices as a whole, and electrical and other components of such analysis devices, which are incapable of causing ignition of a surrounding flammable gas or vapour. With regard to the electrical circuitry, this has the further meaning of one in which any electrical sparking which may occur is incapable of causing such ignition.

According to the present invention, an analysis device comprises an electrically heated analytical element, an intrinsically safe source of electrical energy to heat the element, storage means to accumulate energy from the said source during periods of low load, and control means operable to cause at least partial discharge of the accumulated energy at periods of high load. The analysis device may also have circuits to operate auxiliary and monitoring functions of the device.

In an intrinsically safe circuit, the energy must be restricted, e.g. to below 1 watt and the heating effect of such circuitry may be inadequate. The invention utilizes the storage of energy during periods of low load, and its discharge at occasions of high load to overcome this problem. The means to accumulate energy may be electrostatic or electrochemical, e.g. a capacitor or a battery and it will be seen that with appropriate capacitors or batteries the discharge of accumulated energy may be greater than the input capacity of the intrinsically safe source, although for short periods only.

The control means may be arranged to direct the output of energy from an intrinsically safe source, and/or the discharge of the accumulated energy, when required, to an analytical element and/or to one or more of the auxiliary circuits.

The analytical device may have a plurality of heated analytical elements and/or a plurality of intrinsically safe sources and storage means.

Taking again a chromatographic analysis device as an example, the column, the sample inlet valve and the detector used to detect sample fractions eluting from the column, are to be understood as analytical elements of the invention, providing of course they are heated electrically from an intrinsically safe source and, when necessary, from the storage means, then the detector may be a T.C. (thermal conductivity) or F.I. (flame ionization) detector.

Dealing first with the column, this may be a thin walled metal tube connected to the intrinsically safe source for heating purposes, the heating effect being achieved by virtue of the electrical resistance of the metal of the tube. In the alternative, or possibly in addition, the tube may be resistively heated through a resistance wire winding around its periphery, which wire is connected to the intrinsically safe source.

The tube itself and/or the resistance wire may form one or more arms of an electrical bridge so that the temperature of the tube may be controlled by suitable use of the bridge circuitry in conjunction with the known temperature coefficient of the tube and winding (if present).

The column may be enclosed within a heat insulating material, such as a double walled vacuum flask, the interior of which may be evacuated. The heat insulation will enable the element to be maintained at its operating temperature with the minimum of heat loss thereby requiring the minimum input of electrical energy. By making the heat losses very small, the energy required from the intrinsically safe source can be minimised. The flask may further employ glass wool insulation.

If required by the analysis to be carried out, or by other criteria such as avoidance of condensation of water, the sample injection means and/or the detector may be heated by electrical means powered by an intrinsically safe source. Conventional resistive heating may be used, or the heat may be provided by use of a transistor or integrated circuit which can also serve as a temperature sensor to enable the temperature easily to be controlled.

The analytical elements, the control means and storage means may preferably be kept closely coupled together and may further be encapsulated to the exclusion of air in a rigid body of electrically insulating material such as an epoxy resin.

In operation of the device, the electrical energy required from the source or sources may not be constant, e.g. when a sample for analysis is injected into the column of a chromatograph the load will temporarily increase. By use of the storage means, any excess energy available from the intrinsically safe source in quiescent periods may be accumulated, and then introduced under the control of the control means into the column and/or to one or more of the other analytical elements or auxiliary circuits as required.

The or each intrinsically safe source may be of conventional form comprising mains powered circuitry delivering low voltage DC power via a zener diode barrier circuit such as is described in the present applicant's British patent specification No. 977913.

The source may comprise a support battery or accumulator system so that the analytical device may be portable and independent of a mains supply.

The present invention may be applied to many forms of analytical devices such as those utilizing electric powered quartz crystal and sonic detector systems.

The invention can be embodied in various ways and a specific embodiment will now be described by way of example with reference to the accompanying drawings in which.

Figure 1:
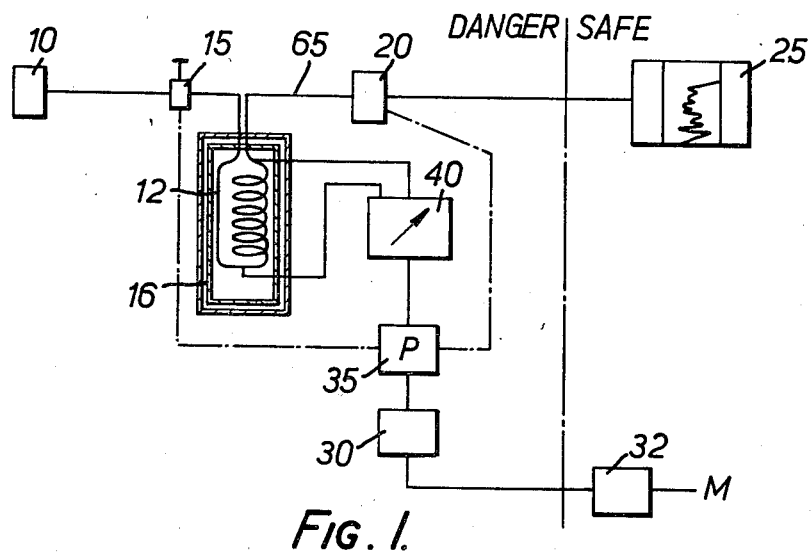
FIG. 1 is a somewhat diagrammatic view of a chromatographic analysis device embodying the invention.

FIG. 1 shows diagrammatically a chromatographic analytical system comprising a carrier gas supply 10 feeding through a chromatographic column 12 encased in a double walled vacuum vessel 16 to a detector element 20 which is in turn connected to a pen recorder printout apparatus 25. A sample injection valve 15 is provided between the carrier gas supply 10 and the column 12. The system is controlled by a control/programmer 35.

The control/programmer 35 is fed from mains via a rectifier (not shown), a zener safety barrier 32 and storage means 30. The rectifier and safety barrier provide an intrinsically safe power supply.

The column 12 is a thin walled metallic chromatographic tube containing active material, and has electrical connections spaced apart along its length. The electrical connections are led off to a Wheatstone bridge circuit 41 (see FIG. 2) associated with a temperature control box 40, the metal column 12 between the electrical connections constituting an arm of the bridge circuit, 41. Adjustment means are provided on the control box 40 which is powered from the control/programmer 35, so that the temperature of the column 12 can be adjusted and set.

In an alternative form (not shown) the temperature of the column 12 is controlled by resistive heating of a resistive wire winding on the outside of the tube, the wire winding forming part of the Wheatstone bridge circuit 41.

Figure 2:
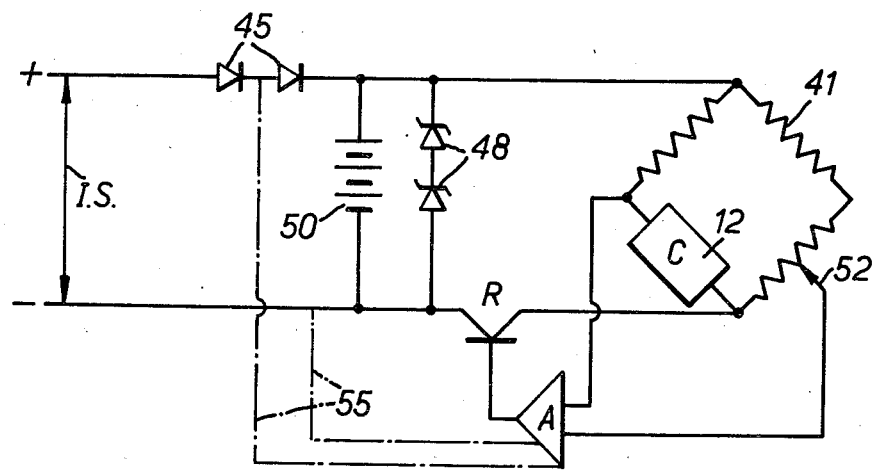
FIG. 2 is an electric circuit for heating the column of FIG. 1.

In FIG. 2 the column 12 is shown forming part of the bridge circuit 41. The circuit comprises two diodes 45, two zener diodes 48 and a battery 50. The diodes 45 prevent a dangerous discharge in the event of a short circuit of the supply lines. The zener diodes 48 prevent overcharging of the battery 50. An adjuster 52 is set on the appropriate arm of the bridge circuit 41 for the required column temperature and the output of the bridge 41 is amplified by the amplifier shown at A which drives the regulator shown at R to adjust the voltage across the bridge necessary to maintain the column 12 at the desired temperature. The battery 50 accumulates power during quiescent periods when little or no energy is required to adjust or maintain the temperature of the column 12. However, if a substantial power requirement occurs, the energy accumulated in the battery discharges to boost the intrinsically safe input and rapidly bring the column 12 to the required temperature. The connections 55 constitute the power for the amplifier in A and are arranged such that when the intrinsically safe power supply fails or is cut off, the regulator R opens and the battery will not discharge through the circuit.

The column 12, its flask 16, and the circuitry shown in FIG. 2 are encapsulated, for example, in an epoxy resinous material (not shown) with appropriate outlet and inlet or output and input connections.

Figure 3:
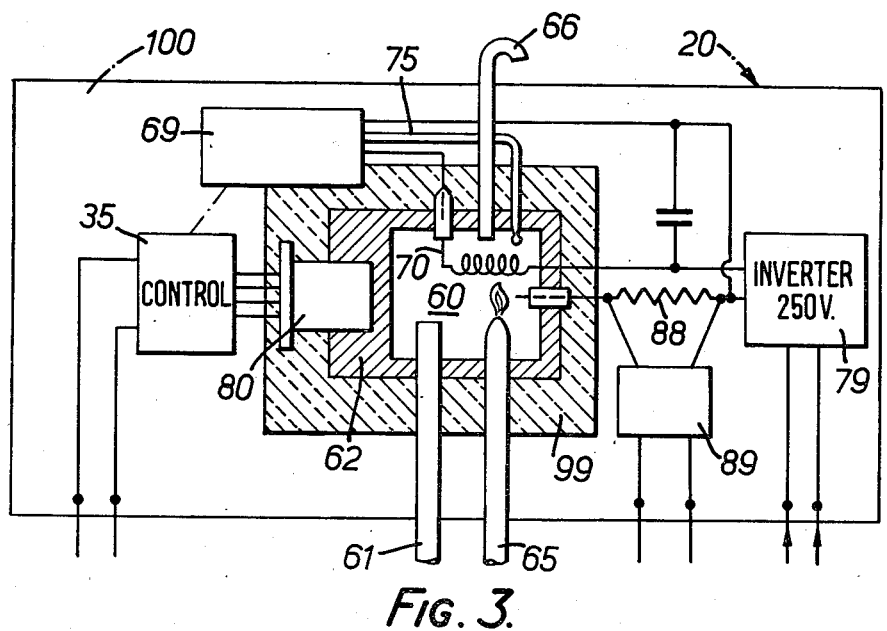
FIG. 3 is a section through a flame ionization detector shown diagrammatically in FIG. 1

FIG. 3 shows a flame ionization detector 20 which comprises an ionization chamber 60, within a block 62 of high conductivity metal, fed by an air inlet 61 and a hydrogen-plus-sample inlet 65, leading from the column 12.

The flame gases are exhausted through a vent 66 to the atmosphere. The tubes comprising these inlets and outlets are capilliary tubes to act as flame traps in the event of an explosion within the chamber 60.

The detector 20 has an ignition system 69 comprising a glow wire 70 by which the hydrogen can be ignited, a "flame out" detector 75, an inverter 79 for the detector and a heating element 80 all powered from the intrinsically safe source 32 via storage means 30. In an alternative not shown, a plurality of sources of intrinsically safe power may be provided.

The ignition system 69, the detector 75 and the heating element 80 are connected to the control/programmer 35. The heater element 80 comprises a transistor or an appropriate integrated circuit and is such as is capable of acting both as a heater and as a temperature sensor whereby the temperature of the metal block 62 may be adjusted to or maintained at a desired temperature.

Alterations in the ionization of the hydrogen flame within the chamber 60 are detected across a resistor 88 in the inverter circuit through a preamplifier 89 (if required) and then to a recorder 25 (see FIG. 1) where the differences in ionization can be represented, e.g. as a pen trace.

The block 62 is encased within a block 99 of thermal insulation and the entire ionization detector 20 is encased in a hard encapsulation of an epoxy resinous material 100.

The sample injection valve 15 (see FIG. 1) is heated in a like fashion by use of a transistor or integrated circuit embedded in a body of high conductivity metal within the valve structure.

The control circuitry of these heating devices may be substantially as described in FIG. 2. The supply for the inverter 79 may comprise a simple zener barrier circuit with or without suitable storage means.

Figure 4:
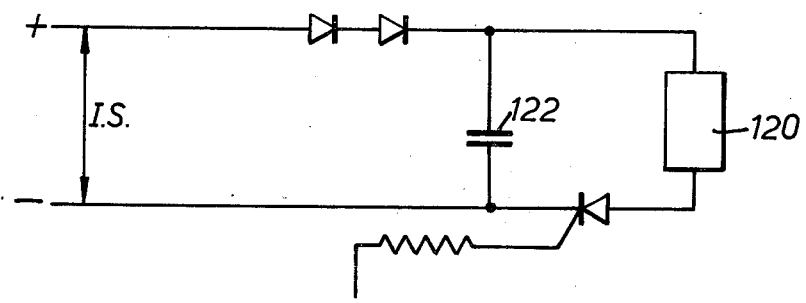
FIG. 4 is a further electric circuit for heating other items of the device of FIG. 1.

The glow wire and other intermittently operated devices such as a solenoid controlled injection valve may be controlled by a circuit as shown in FIG. 4 where 120 represents the glow wire or solenoid. The circuit has a capacitor 122 which acts in the manner of the above described storage means.

Referring again to the sample injection valve 15, this may comprise a solenoid controlled valve (not shown) such as is described in the present applicant's British patent specification No. 1466246, or alternatively other forms of mechanical or intrinsically safe electrically operated valves may be used. The sample injection valve 15 is preferably thermally insulated and controlled.

What I claim as my invention and desire to secure by Letters Patent is:

1. An intrinsically safe chromatographic analysis device to be encapsulated in a rigid body of electrically insulating material, said device having input connections for supply to said device from a source of electric power, and output connections to transmit analysis data from said device to remote monitoring means;

said device further comprising at least one electrically heated analytical element, intrinsically safe electrical energy supply means electrically connected between said input connections and said at least one electrically heated analytical element;

said supply means incorporating storage means to accumulate energy from the said source during periods of low electrical load and control means operable to cause at least partial discharge of the accumulated energy at periods of high electrical load.

2. A chromatographic analysis device as claimed in claim 1 wherein the discharge rate of accumulated energy is greater than the steady output of the said source.

3. A chromatographic analysis device as claimed in claim 1 wherein auxiliary circuits of the device are also fed with energy from the said supply means.

4. A chromatographic analysis device as claimed in claim 3 wherein the control means direct the output of the said supply means, and the discharge of the said accumulated energy, when required, to the analytical element and/or to one or more of the auxiliary circuits.

5. A chromatographic analysis device as claimed in claim 3 having a heated sample injection means connected to an auxiliary circuit and fed with energy from said source through said auxiliary circuit.

6. A chromatographic analysis device as claimed in claim 3 having a heated sample fraction detector analytical element connected to an auxiliary circuit and fed with energy from said source through said auxiliary circuit.

7. A chromatographic analysis device as claimed in claim 1 in which the analytical element is enclosed within heat insulating material.

8. A chromatographic analysis device as claimed in claim 7 wherein the analytical element comprises a chromatograph column contained within a double walled vacuum flask.

9. A chromatographic analysis device as claimed in claim 1 wherein the analytical element comprises a chromatograph column comprising a metal tube electrically connected to the said supply means to allow heating by virtue of its own electrical resistance.

10. A chromatographic analysis device as claimed in claim 9 wherein the column forms one or more arms of an electrical bridge.

* * * * *